(12) United States Patent
Kalender

(10) Patent No.: US 7,500,783 B2
(45) Date of Patent: Mar. 10, 2009

(54) METHOD FOR RECORDING IMAGES OF A DEFINABLE REGION OF AN EXAMINATION OBJECT USING A COMPUTED TOMOGRAPHY FACILITY

(75) Inventor: Willi Kalender, Möhrendorf (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/901,668

(22) Filed: Sep. 18, 2007

(65) Prior Publication Data
US 2008/0075225 A1 Mar. 27, 2008

(30) Foreign Application Priority Data
Sep. 22, 2006 (DE) .................... 10 2006 044 783

(51) Int. Cl.
H05G 1/02 (2006.01)
(52) U.S. Cl. ....................... 378/197; 378/205
(58) Field of Classification Search ............... 378/4–20, 378/196–197, 205, 62
See application file for complete search history.

(56) References Cited

U.S. PATENT DOCUMENTS

| 4,894,855 A | 1/1990 | Kresse | |
| 6,246,742 B1 * | 6/2001 | Besson et al. | 378/8 |
| 2003/0076920 A1 | 4/2003 | Shinno et al. | |
| 2003/0235266 A1 * | 12/2003 | Gregerson et al. | 378/4 |
| 2004/0066907 A1 * | 4/2004 | Fadler | 378/197 |
| 2006/0198499 A1 | 9/2006 | Spies et al. | |

FOREIGN PATENT DOCUMENTS

| DE | 199 58 864 A1 | 6/2001 |
| EP | 0220501 B1 | 5/1987 |

* cited by examiner

Primary Examiner—Hoon Song

(57) ABSTRACT

There is described a method for recording images of a definable region of an examination object using an x-ray diagnostics facility for producing computed tomography recordings comprising an image recording facility comprising at least one radiation source and at least one radiation detector for the rotating recording of individual images, on the basis of which an image suitable for outputting is produced, comprising the following steps: Recording of images of the entire examination region by rotating the image recording facility about a first isocenter with a first measuring field, a first resolution and a first dose, and generating an overview image of the examination object; Defining the region in the examination object based on the overview image and defining the location of a second isocenter as a function of the location and/or geometry of the region.

19 Claims, 2 Drawing Sheets

METHOD FOR RECORDING IMAGES OF A DEFINABLE REGION OF AN EXAMINATION OBJECT USING A COMPUTED TOMOGRAPHY FACILITY

CROSS REFERENCE TO RELATED APPLICATIONS

This application claims priority of German application No. 10 2006 044 783.2 DE filed Sep. 22, 2006, which is incorporated by reference herein in its entirety.

FIELD OF INVENTION

The invention relates to a method for recording images of a definable region of an examination object using an x-ray diagnostics facility for producing computed tomography recordings, a computed tomography facility, comprising an image recording facility comprising at least one radiation source and at least one radiation detector for the rotating recording of individual images, on the basis of which an image suitable for outputting is produced.

BACKGROUND OF INVENTION

It is known that it is possible with a computed tomography facility, due to the rotation of the image recording facility, to record a plurality of individual images of the examination object from different directions. These individual images are then processed using an image processing facility in such a manner that a reconstruction image suitable for outputting, generally a 3D reconstruction image, can be generated and displayed. In the context of the present invention the term x-ray diagnostics facility for producing computed tomography recordings, shortened to computed tomography facility, is used to refer to both conventional computed tomography systems, which have a fixed gantry with a rotating image recording facility—whether in the form of a rotating emitter-detector unit or in the form of just a rotating emitter with a fixed detector ring—as well as x-ray facilities, for example with a C-arm, on which the radiation source and radiation detector are disposed and which can rotate about the examination object. The structure and mode of operation of computed tomography facilities of both types are sufficiently known.

To produce a computed tomography image a first recording or first scan is first carried out with a low radiation dose and low detector resolution, which can be achieved for example in the context of image processing by pixel binning, in order to obtain an overview image, which allows a first general overview or initial diagnosis. The user can then orient themselves within this overview image and select a defined region, which requires closer consideration, to which end a second recording or second scan is carried out. This defined region is now generally away from the center of the image and therefore away from the isocenter, about which the image recording facility of the computed tomography facility rotates. When the second recording or second scan is now carried out, it is done with a significantly higher dose and a higher resolution on the part of the detector, to record the image so that it is as informative as possible and it is possible to show even fine structures with sufficient clarity and contrast. It is possible to reduce the measuring field to some degree based on the maximum size in the context of the first recording. However since the image recording facility also rotates about the same isocenter during the second recording, the measuring field reduction is limited, as it must be ensured that the measuring field captures the region of interest in every instance from any recording direction. As a result the radiation load on the examination object in regions away from the defined region of actual interest is considerably high due to the necessarily relatively large measuring field during this second scan. Also the recorded image data set per individual image is considerably large due to the large measuring field.

SUMMARY OF INVENTION

The invention is therefore e.g. based on the problem of specifying a method, which opens up the possibility of recording with high resolution a defined region, which is located at any position in the examination object, with a low dose load for the patient.

To resolve this problem a method with the following steps is provided according to the invention:

Recording of images of the entire examination region by rotating the image recording facility about a first isocenter with a first measuring field, a first resolution and a first dose, and generating an overview image of the examination object, Defining the region in the examination object based on the overview image and the location of a second isocenter as a function of the location and/or geometry of the region and Automatic positioning of the image recording facility in respect of the second isocenter and recording of images of the region by rotating the image recording facility about the second isocenter with a reduced second measuring field defined automatically as a function of the geometry of the region, a higher second resolution and a second dose, and generating and outputting a region image showing the region with high resolution.

With the inventive method an overview image is first recorded, as has been standard practice to date. A scan is carried out here with a maximum measuring field, the standard low resolution selected in the context of an overview image and a low radiation dose. The defined region, which is to be recorded with high resolution, is then defined within this overview image. This is for example an organ or a bone, for example a vertebral body, or an implant, etc. This region can also be defined in a different manner, either manually by the user by corresponding positioning of a marking defining or selecting the region on a monitor outputting the overview image, with the marking being acquired by computer and the limits of the region being defined as a function of the marking positions, or automatically by means of an automatic image analysis after predetermination of the region to be determined, the type or geometry of which is defined beforehand. This is described in more detail below.

When the region has been defined per se and in respect of its location in the overview image and therefore also in the coordinate system of the computed tomography facility, a second isocenter is defined, which is determined as a function of the location and/or geometry of the previously defined region, just as this was defined. This second isocenter lies within the defined region, so that said region itself lies within the isocenter as if in the context of a recording to be carried out subsequently, therefore is positioned ideally in respect of the image recording facility, which rotates about it as a center point.

After the second isocenter has been determined, the image recording facility is then automatically repositioned in respect of the second isocenter; thus it is positioned so that it rotates about precisely this isocenter in the context of a subsequent recording. The invention makes use here of the fact that in the meantime computed tomography facilities have become known, which in principle allow relative movement of the image recording facility in relation to the examination object, which is lying in a fixed position on a patient support. Such a computed tomography facility in the form of a C-arm x-ray facility with a rotating C-arm is known for example from DE 199 58 864 A1. The C-arm is disposed on a support frame in the manner of a robot arm, being disposed on said support frame in such a manner that it can be rotated about a horizontal axis. Said support frame in principle allows variation of the position of the C-arm and therefore the image recording facility on the C-arm in relation to the patient support. This relative movement is utilized by the inventive method, wherein the image recording facility is now positioned precisely in such a manner that the axis of rotation of the image recording facility, therefore the horizontal axis of rotation of the C-arm, lies precisely in the second isocenter, which passes through the defined region.

In the next step the second recording or second scan is carried out, with the image recording facility now rotating about the second isocenter. In contrast to during the first recording or first scan however the second measuring field has been tailored to the location/geometry of the region, which now lies within the isocenter, and is therefore significantly reduced compared with the first measuring field. This is possible, since now the region of interest lies within the isocenter, therefore on the central beam of the radiation source. The second measuring field can now be reduced to an extreme degree; ultimately its size is primarily only a function of the three-dimensional geometry of the region or its size. A relatively small region, for example a vertebra, can therefore be recorded with an extremely small measuring field, which is selected to be of such a size that it still captures the vertebra completely in any recording position.

In addition to the significantly reduced measuring field, the detector resolution is also changed. Recording now takes place or the subsequent image is produced with a high detector resolution. The image is also recorded with a second dose, which can either correspond to the first dose, in other words can be relatively low, it being possible to select the level of the dose in some instances as a function of the region or object to be recorded. It is of course also possible to record the image with a much higher second dose than the first dose, in some instances with the highest possible dose, if this is necessary for high-resolution image recording or as a function of the region/object to be recorded.

The inventive method permits the recording of a region of interest, in other words a defined three-dimensional volume of interest in a very simple manner, in conjunction with a significantly lower radiation load for the patient due to the inventive repositioning of the image recording facility in respect of a second isocenter and the inventive tailoring of the measuring field. If recording is carried out with the same radiation dose as in the context of the first recording with a large measuring field, the radiation load must be smaller, since the object regions away from the region of interest within the isocenter are only exposed to direct radiation to a minor degree, in contrast to the large, maximum measuring field. If a high or the highest possible dose is used in the context of the second recording, the radiation load is also significantly smaller for this reason, compared with a high-dose image recording with the significantly larger measuring field according to the prior art with just one isocenter.

As described above, the size of the second measuring field is preferably defined automatically, as soon as the location of the region of interest has been defined in the overview image and therefore its coordinates, as well as in its three-dimensional form. The control facility is able to determine the location of the new isocenter directly and to define the size of the second measuring field as a function of the defined region limits. Corresponding collimation of the radiation source then takes place, in other words the shutters of the radiation source are adjusted accordingly, so that the emitted radiation fan corresponds to the predefined measuring field.

According to a first alternative of the invention the region can be defined on the user side within the overview image output on a monitor by means of a computer-controlled marking means, with the second isocenter and second measuring field being defined automatically based on the marking data. The user for example draws in a marking line or similar using the screen cursor in the overview image, to define the region, for example an organ or bone, etc. in this manner. The line defines the limits of the region, as a function of which the second isocenter and second measuring field are determined. The individual image positions are correlated with the coordinate system of the computed tomography facility, so that there is a unique relationship between the marking and therefore the information relating to the region and the coordinate system, so that the second isocenter and measuring field can be defined with positional accuracy.

In an alternative selection option the type and/or geometry of the region to be defined are selected or specified on the user side by way of an input means, after which the region within the overview image is automatically defined with computer assistance based on information about the type and/or geometry and the second isocenter and second measuring field are determined based on the result of the definition. The user is for example shown different pictograms or similar selection elements (icons) on the monitor, which define different organs or different bone structures or implants, etc. for example. If a vertebra is to be selected as the region for example, the user can click on a corresponding icon showing a vertebra, whereupon an automatic analysis algorithm searches for a corresponding structure in the overview image. It is possible here for example to use an edge detection algorithm, which can determine corresponding contrast edges in the overview image. Once the corresponding structure in the overview image has been determined, the control facility determines the location of the new isocenter, the corresponding new position data for the image recording facility, in order to be able then to move this automatically into the corresponding position, and the second measuring field to carry out collimation by varying the shutter position.

The overview image and the region image can be output together, so that the user can on the one hand see the entire examination region in an adequate display that allows a general overview and can also obtain information in a high or maximum-resolution form relating to the region of interest from the second image. Information relating to the region away from the region of interest, which due to the very small measuring field is not shown in the region image with the same resolution as the overview image, can be removed from the overview image without further ado.

In a development of the invention image regions in the region image, which show regions of the examination object away from the defined region, are replaced with image regions segmented from the overview image. In other words both images, the overview image and the region image, can in some instances be merged to a certain extent, in that the image regions shown in the region image with inadequate resolution or contrast due to the very small measuring field are replaced with corresponding image regions, which are segmented from the overview image and which are of better image quality in comparison. This results in what is almost a combination image with the best possible information content.

The image information of the overview image from image regions away from the defined region and relating to image quality can also be taken into account when generating the region image. If for example certain artifacts are known from the overview image, which are in some instances also disruptive in the region image, it is possible to correct said artifacts in the region image, preferably those influencing the display of the region of interest, by corresponding image post-processing.

So that the resolution at the radiation detector can be varied as simply as possible, a radiation detector with a higher number of pixels in the region of the center of the detector than in the adjoining regions can be used. The center region lies on the central beam of the radiation source. This results in something like an "x-ray lens", since the overview or region image can have higher resolution in this region.

In the case of large regions of interest and also where the scan paths are below 360°, artifact-free reconstruction can be enabled, if the first measuring field with the first resolution is made up of at least two individual measuring fields respectively to form an extended two-dimensional measuring field according to the earlier patent application 10 2006 041 033.5, with the at least two individual measuring fields respectively being recorded with a constant relative position between the focus of the radiation source and the region of interest.

Increased movement capacity is possible, when the at least one radiation source and/or the at least one radiation detector for the rotating recording of individual images are attached to a support arm in the manner of a robot arm according to EP 0 220 501 B1.

Alternatively according to the invention the at least one radiation source and the at least one radiation detector for the rotating recording of individual images can be attached to a C-arm held by a support arm in the manner of a robot arm according to DE 199 58 864 A1.

In general the inventive method allows high-speed recording of a low-resolution overview image recorded with a low dose with a large measuring field, followed by the maximum-resolution recording of any small region of interest with a minimal measuring field and any high, even the maximum dose without having to move the patient due to the capacity of the image recording facility to be moved to allow rotation about a second isocenter. This allows any structures in the overview image to be displayed at high speed with maximum resolution, for example organs or bone structures or even implants, such as an inserted stent, etc. The radiation load for the patient is minimal however.

BRIEF DESCRIPTION OF THE DRAWINGS

Further advantages, features and details of the invention will emerge from the exemplary embodiment described below and the drawings, in which.

DETAILED DESCRIPTION OF INVENTION

Figure 1:
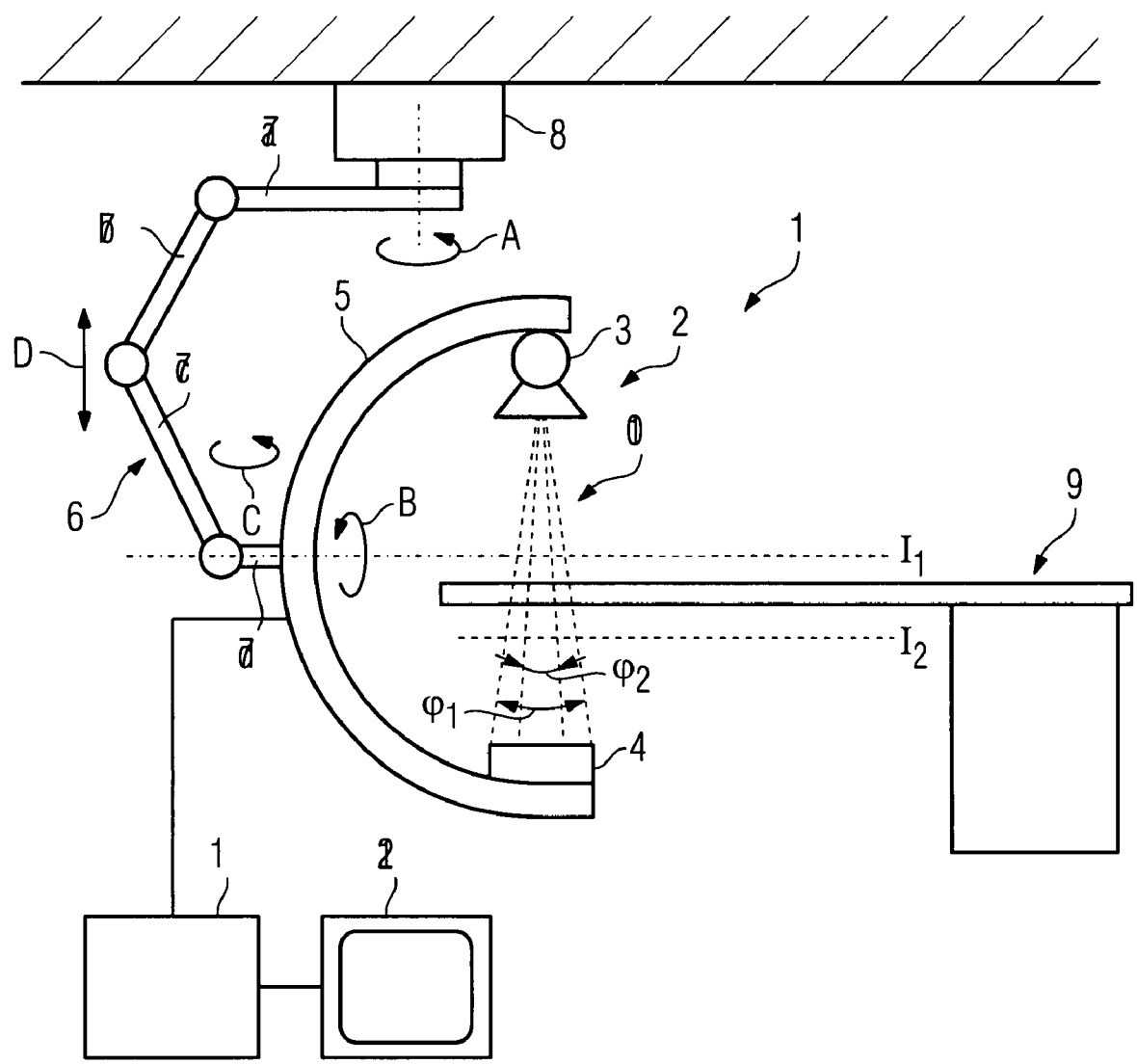
FIG. 1 shows a basic diagram of a computed tomography facility, suitable for implementing the inventive method.

FIG. 1 shows a computed tomography facility 1, comprising an image recording facility 2, comprising a radiation source 3 and a radiation detector 4, for example in the form of a solid detector. The radiation source 3 and radiation detector 4 are disposed on a C-arm 5, which is in turn disposed on a support arm structure 6 in the manner of a robot arm, which in the example shown consists of four arms 7a, 7b, 7c and 7d, which are linked to each other by way of corresponding joints. The arm 7a is disposed on a ceiling-side support 8, on which it is disposed in such a manner that it can be rotated about a first axis of rotation, shown by the arrow A. The C-arm is disposed on the support arm 7d in such a manner that it can be rotated about a horizontal axis B, in order to be able to record computed tomography images by rotating the image recording facility 2, and it can also be pivoted as required about a vertical axis, as shown by the arrow C. The support arm structure 6 allows a vertical movement of the C-arm 5 and therefore the image recording facility 2, as shown by the double arrow D, so that said image recording facility 2 can be displaced vertically in relation to a patient on a patient support 9. In conjunction with the capacity of the C-arm 5 to move about the axes of rotation A and C a lateral displacement can also be achieved, so that there is in principle free movement in each of the three spatial directions. This allows the isocenter, through which the rotating arm rotates about the axis of rotation B during computed tomography image recording, to be displaced. In the example shown a first isocenter $I_1$ is shown by way of example, about which the C-arm 5 and therefore the image recording facility 2, rotates in the first position shown. If the C-arm 5 were moved downward vertically for example by way of the support arm frame 6, it would rotate about the second isocenter $I_2$. The relative position in respect of the patient in the same position on the patient support 9 would therefore be changed.

Also shown is the radiation fan 10 emitted by the radiation source 3, which penetrates the object on the patient support 9 during the rotating scan and is absorbed by the radiation detector 4. As shown by way of example in FIG. 1 it is in principle possible to vary the angle of the radiation fan, it being possible to reduce the fan angle without further ado from a maximum fan angle $\phi_1$, as shown by the second radiation fan angle $\phi_2$. This fan or opening angle is used to define the size of the measuring field, in other words the field or region of the examination object, which is always penetrated by radiation in every recording during the rotating image recording.

Also provided is a control facility 11, which controls the entire movement and image recording operation of the computed tomography facility 1. It therefore controls both the movement of the support arm frame 6 and the C-arm rotation, as well as operation of the image recording facility 2. It also reads out the image signals generated on the detector side and processes these to produce computed tomography images that are suitable for outputting, whether two-dimensional or three-dimensional, and outputs these on an assigned monitor 12.

Figure 2:
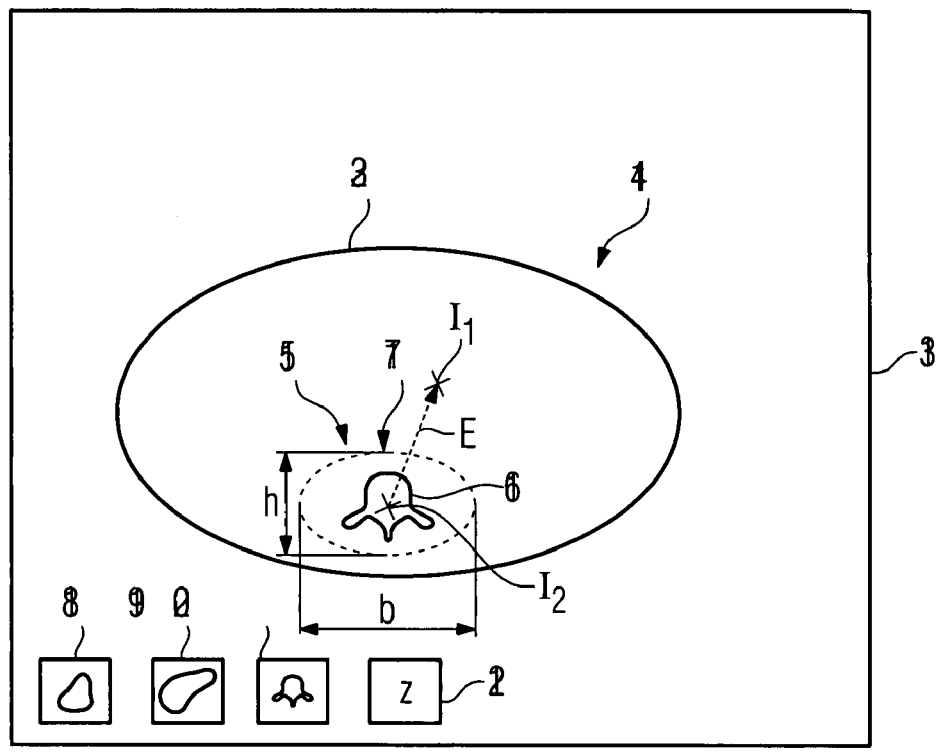
FIG. 2 shows a basic diagram of an overview image, obtained after a first recording, describing the selection of a defined region to be recorded with high resolution.

As described, with the inventive method a first overview image is recorded first, as shown by way of example in FIG. 2. The overview image 13 here shows a two-dimensional representation of the examination object 14. It was recorded by rotating the image recording facility 2 about the first isocenter $I_1$; this is shown in the overview image 13 and lies in the center of the image. The overview image 13 was recorded with a large, generally the maximum measuring field, in other words with a maximum fan angle $\phi_1$. The detector resolution is low, since it is only a matter of obtaining a first general overview of the examination object 14. The radiation dose used is also very low, in order to keep the overall load for the patient low.

In a next step a region of interest 15 is defined in the overview image 13 or in the examination object 14 shown therein. In the example shown, a vertebra 16 is shown, which because it is damaged, is to be recorded and displayed in a second high-resolution display with the greatest possible detail and contrast so that it can be analyzed very readily for diagnostic purposes. There are various possibilities for selection, shown as alternatives in FIG. 2. On the one hand it is possible to define the region 15 by way of a marking means 17, in this instance in the form of a line shown broken around the vertebra 16. The user can draw in this line, for example as a geometric object by way of a corresponding software application option using the screen cursor. This line is used to define the limits of the region. In the example shown the marking means 17, in other words the line, is an ellipse of width b and height h. Of course it is also possible to draw the line as a circular line with a regular diameter. In any case this marking means 17 serves to define the location and size and respectively the geometry of the selected region 15, as a function of which parameters a second isocenter $I_2$ and the size of the fan angle $\phi_2$ to be newly set are then defined.

As an alternative to drawing in the marking means 17 manually, different icons 18, 19, 20 are shown in FIG. 2. The icon 18 is intended to symbolize a heart for example, the icon 19 a liver and the icon 20 the vertebra 16. In the example shown the user can use the cursor to select the icon 20. The control facility 11 now uses a corresponding analysis algorithm to analyze the overview image 13, to determine a corresponding structure, in other words the vertebra 16, stored or defined using software by way of the icon 20. This is done for example by way of an edge detection algorithm, etc. In this instance the precise geometry of the region of interest 15 is defined. The location of this region and its geometry also serve here to define the second isocenter $I_2$ and the second fan angle $\phi_2$ for a subsequent image recording.

Also provided is a further icon 21, marked "z". This icon z serves to define the depth of the region of interest 15 in the z-direction. In other words the two-dimensional geometry, as shown in the overview image 13 shown here in two dimensions, and data in the z-direction are used to define the volume of interest, which is to be scanned by way of the radiation fan. This definition of the extent of the volume of interest in the z-direction is necessary irrespective of the manner of determining the region of interest, whether this is manual or automatic.

When the region of interest 15 has been defined, the location of the new, second isocenter $I_2$ and the fan angle $\phi_2$ are defined on the part of the control facility 11. In the example shown geometric information about the region 15, in this instance for example the width b and the height h, are used to define the isocenter and fan angle. The fan angle $\phi_2$ must be so great that it captures the region completely from any recording direction; therefore at least the width b must be acquired. The location of the isocenter $I_2$ is determined using the geometry of the region. When the marking means 17 is drawn in for example, the center point of the ellipsoid is defined here; this is at b/2 and h/2.

Based on these results for the second isocenter $I_2$ and the second fan angle $\phi_2$ the control facility 11 now defines both the control parameters for moving the support arm joint 6 and the C-arm 5, to position the C-arm 5 and therefore the image recording facility 2 in such a manner that it rotates precisely about the newly determined second isocenter $I_2$ and so that this therefore lies in the center of the image. The control facility 11 also determines the new collimation of the radiation source 3, to adjust the measuring field so that only the region of interest is scanned from every irradiation direction and so that the fan angle $\phi_2$ is therefore adjusted in conjunction with the length information in the z-direction. This is done by corresponding automatic adjustment of the shutters of the radiation source 3.

In the next step the image recording facility 3 is positioned by corresponding activation of the positioning motors, by way of which the support arm frame 6 and the C-arm 5 can be moved, so that it can rotate about the second isocenter $I_2$ and the shutters are adjusted to the position defining the fan angle $\phi_2$.

Figure 3:
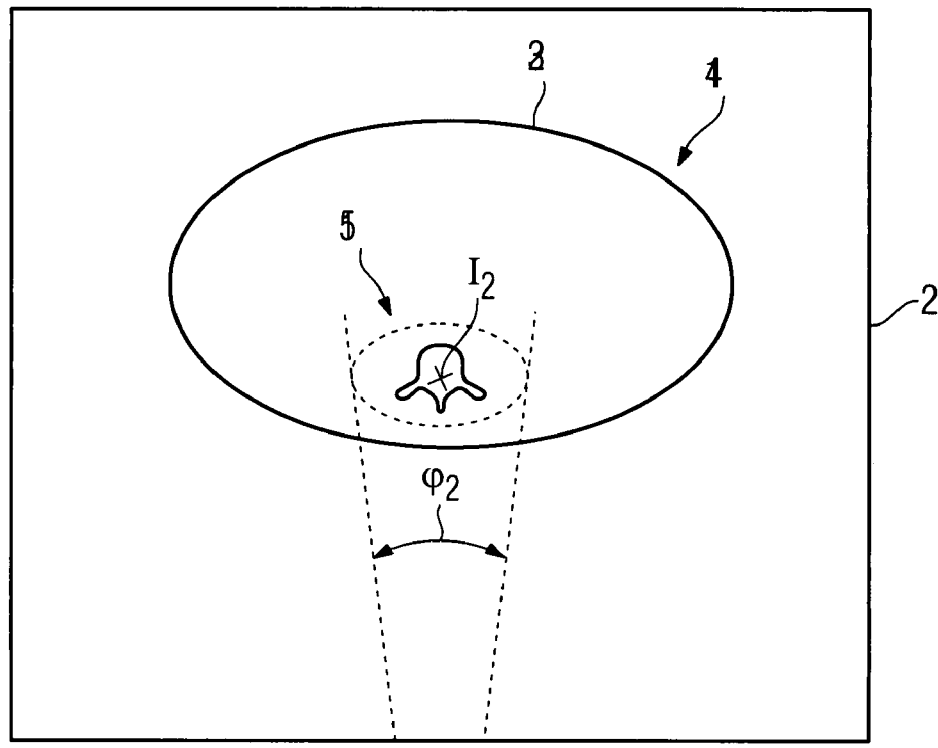
FIG. 3 shows a region image with the region selected according to FIG. 2 in the isocenter.

In the next step a second image is recorded. The resulting region image 22 is shown in FIG. 3. As can be seen, the selected region 15 is now in the center of the image, as shown by the second isocenter $I_2$. Also shown is the second fan angle $\phi_2$, shown from a defined irradiation direction. The examination object 14 itself lies asymmetrically in respect of the center of the image, since the isocenter 2 has been displaced into the center of the image, where the isocenter 1 was previously located, as shown by the arrow E shown broken in FIG. 2.

The region image 22 was recorded with high or maximum detector resolution, the measuring field defined by way of the fan angle $\phi_2$ is significantly reduced compared with the maximum measuring field defined by way of the fan angle $\phi_1$ and tailored optimally to the actual size of the region of interest. The dose can be the same as for recording the overview image or it can be greater or a maximum, depending on what is required for recording or diagnostic reasons.

Both the overview image 13 and the region image 22—of which a number of successive recordings or scans can of course be acquired—can be output together on the monitor 12, so that the user can look at both sets of image information at the same time. In the overview image 13 the information relating to the object region 23 away from the region of interest 15 is in some instances clearer and more easily identifiable than in the overview image 22, since it was recorded with an extremely small fan angle and therefore an extremely small measuring field, so that the object regions, which form the image 23, were not directly irradiated often as they were when the overview image was recorded with a large fan angle. It is also possible to segment the image region showing the region 23 in the overview image from this and insert it into the region image 22 instead of the original region 23. A combination image would then be output on the monitor 12, wherein the region 23 originates from the overview image, while the region 15 recorded with extremely high resolution and the smallest focus and maximum dose with an extremely small measuring field originally comes from the region image 22.

As described above, the computer determination or generation of the overview image 13 and region image 22 takes place by way of the control facility 11. This can now take into account information relating to image disruption such as artifacts or similar present in the overview image 13 when generating the region image 22 and correct this for example in the context of image preparation or image post-processing in respect of said artifacts or other inhomogeneities in the image, so that the most artifact-free region image 22 possible can be output. Since it is the region of interest 15 in particular, which is recorded and displayed with maximum resolution, in the region image 22, the artifacts that disrupt this region are to be taken into account primarily.

To allow the resolution to be varied, it is possible to use a radiation detector 4, which has a higher number of pixels per square centimeter in the region of the center of the detector than in adjoining regions. The central region of the detector always lies in the central beam of the radiation source 3, therefore always in the radiation fan, regardless of the latter's opening angle. Since according to the invention the region of interest 15 lies in the second isocenter $I_2$ in the context of the second recording, this region 15 is therefore mapped in the central detector region with the high number of pixels per square centimeter and can therefore be displayed with very high resolution, without the resolution being varied for example by pixel binning on the part of the computer.

The invention claimed is:

1. A method for recording images of a definable region of an examination object using an x-ray diagnostics facility for producing computed tomography recordings, comprising:
    providing an image recording facility having at least one radiation source and at least one radiation detector of the type which generates images of objects by rotating about a center of rotation definable as an isocenter with respect to the object;
    recording images of the entire examination region by rotating the image recording facility about a first isocenter, wherein the first isocenter is the center of rotation of the recording facility, with a first measuring field, a first resolution and a first dose, and generating an overview image of the examination object;
    defining a region in the examination object based on the overview image and defining a second isocenter at a location different from the first isocenter based upon a feature of the region, wherein the feature is selected from the group consisting of the location of the region, the geometry of the region, and a combination thereof;
    re-positioning the image recording facility to displace the center of rotation of the facility with respect to the object from the first isocenter to the second isocenter without requiring movement of the examination object from a fixed position on a support;
    recording images of the region by rotating the image recording facility about the second isocenter; and
    generating a region image showing the region.

2. The method as claimed in claim 1, wherein images are recorded about the second isocenter with a reduced second measuring field defined automatically based upon the geometry of the region, a higher second resolution and a second dose so that the region image showing is outputted with higher resolution than provided by rotating the image recording facility about the first isocenter.

3. The method as claimed in claim 1, wherein the second dose is higher than the first dose.

4. The method as claimed in claim 1, wherein the region is defined by a user within an overview image output on a monitor using a computer-controlled marking procedure.

5. The method as claimed in claim 4, wherein the second isocenter and the second measuring field are defined automatically based on data of the marking procedure.

6. The method as claimed in claim 3, wherein the region is defined by a user within an overview image output on a monitor using a computer-controlled marking procedure.

7. The method as claimed in claim 6, wherein the second isocenter and the second measuring field are defined automatically based on data of the marking procedure.

8. The method as claimed in claim 1, wherein a type of the region to be defined is selected or specified on a user side based on an input, wherein after the input the region within the overview image is automatically defined with computer assistance based on information about the type, and wherein the second isocenter and second measuring field are determined based on the result of the definition.

9. The method as claimed in claim 1, wherein a geometry of the region to be defined is selected or specified on a user side based on an input, wherein after the input the region within the overview image is automatically defined with computer assistance based on information about the geometry, and wherein the second isocenter and second measuring field are determined based on the result of the definition.

10. The method as claimed in claim 1, wherein the overview image and the region image are output together.

11. The method as claimed in claim 1, wherein image regions in the region image showing regions of the examination object away from the defined region, are replaced with image regions segmented from the overview image.

12. The method as claimed in claim 1, wherein image information of the overview image from image regions away from the defined region and relating to image quality are used for generating the region image.

13. The method as claimed in claim 1, wherein the first measuring field with the first resolution has at least two individual measuring fields to form an extended two-dimensional measuring field, wherein images are recorded with the at least two individual measuring fields with a constant relative position between the focus of the radiation source and the region of interest.

14. The method as claimed in claim 1, wherein the radiation source is attached to a robot arm for the rotating recording of individual images.

15. The method as claimed in claim 1, wherein the radiation detector is attached to a robot arm for the rotating recording of individual images.

16. The method as claimed in claim 1, wherein the radiation source and the radiation detector are attached to a C-arm held by a support arm for the rotating recording of individual images.

17. The method as claimed in claim 16, wherein a robot arm is used as the support arm.

18. The method as claimed in claim 16, wherein a plurality of radiation sources are attached to the C-arm.

19. The method as claimed in claim 16, wherein a plurality of radiation detectors are attached to the C-arm and the C-arm is both rotatable about a horizontal axis and displacable in at least one spatial directions to effect movement between the first and second isocenters without requiring movement of the examination object.

* * * * *